(12) United States Patent
Leidig

(10) Patent No.: US 8,234,769 B2
(45) Date of Patent: Aug. 7, 2012

(54) DEVICE AND METHOD FOR MOUNTING A NEEDLE GUARD ON A SYRINGE BODY

(75) Inventor: Juergen Leidig, Frankenhardt (DE)

(73) Assignee: Robert Bosch GmbH, Stuttgart (DE)

( * ) Notice: Subject to any disclaimer, the term of this patent is extended or adjusted under 35 U.S.C. 154(b) by 722 days.

(21) Appl. No.: 12/305,754

(22) PCT Filed: Sep. 6, 2007

(86) PCT No.: PCT/EP2007/059314
§ 371 (c)(1),
(2), (4) Date: Dec. 19, 2008

(87) PCT Pub. No.: WO2008/037575
PCT Pub. Date: Apr. 3, 2008

(65) Prior Publication Data
US 2010/0162548 A1   Jul. 1, 2010

(30) Foreign Application Priority Data

Sep. 28, 2006 (DE) .......................... 10 2006 045 926
Oct. 20, 2006 (DE) .......................... 10 2006 049 528

(51) Int. Cl.
*B65B 7/28* (2006.01)
(52) U.S. Cl. ........... 29/456; 29/777; 29/407.08; 29/240; 29/281.5; 53/367
(58) Field of Classification Search ............. 29/407.05, 29/407.08, 407.09, 525, 428, 709, 718, 240, 29/281.5, 777, 456; 156/556; 279/16, 18; 53/287, 367, 306, 308, 310, 341, 342
See application file for complete search history.

(56) References Cited

U.S. PATENT DOCUMENTS

| | | | | | |
|---|---|---|---|---|---|
| 2,765,606 | A | * | 10/1956 | Brown | 53/202 |
| 2,823,500 | A | * | 2/1958 | Brown | 53/53 |
| 2,824,361 | A | * | 2/1958 | Brown | 29/777 |
| 2,841,937 | A | * | 7/1958 | Miskel et al. | 53/276 |
| 2,996,105 | A | * | 8/1961 | Holderith | 156/423 |
| 2,998,050 | A | * | 8/1961 | Hamilton et al. | 156/378 |
| 3,267,567 | A | * | 8/1966 | Shields | 29/777 |
| 3,503,113 | A | * | 3/1970 | Lagsdin | 29/777 |
| 3,597,826 | A | * | 8/1971 | Shields | 29/777 |

(Continued)

FOREIGN PATENT DOCUMENTS

WO   9000414 A1   1/1990

*Primary Examiner* — David Bryant
*Assistant Examiner* — Jason L Vaughan
(74) *Attorney, Agent, or Firm* — Ronald E. Greigg

(57) ABSTRACT

The invention relates to a device for mounting a needle guard onto a syringe body that is provided with a needle. The device includes a retaining device for retaining the syringe body, a needle guard receptacle for receiving the needle guard, a compressed air system for providing compressed air, a first displacement device for displacing the needle guard receptacle in a vertical direction, and a rotation device for at least partially rotating the needle guard receptacle. The needle guard receptacle is disposed beneath the retaining device while the compressed air is fed to the needle guard receptacle such that the needle guard is suspended on an air cushion in a floating manner. The needle guard receptacle can be displaced in a vertical direction by the first displacement device. The invention further relates to a method for mounting the needle guard onto the syringe body.

18 Claims, 4 Drawing Sheets

U.S. PATENT DOCUMENTS

| | | | | |
|---|---|---|---|---|
| 3,662,517 A * | 5/1972 | Tascher et al. | | 53/282 |
| 3,683,483 A * | 8/1972 | Klettke | | 29/777 |
| 3,708,945 A * | 1/1973 | Klettke | | 53/471 |
| 3,801,291 A * | 4/1974 | Shields | | 29/777 |
| 3,807,119 A * | 4/1974 | Shields | | 53/471 |
| 4,118,914 A * | 10/1978 | Shields | | 53/282 |
| 4,271,587 A * | 6/1981 | Shields | | 29/809 |
| 4,628,969 A * | 12/1986 | Jurgens et al. | | 141/1 |
| 4,718,463 A * | 1/1988 | Jurgens et al. | | 141/11 |
| 4,915,698 A | 4/1990 | Levenson | | |
| 5,024,666 A | 6/1991 | Pituch | | |
| 5,078,696 A * | 1/1992 | Nedbaluk | | 604/192 |
| 5,373,684 A * | 12/1994 | Vacca | | 53/425 |
| 5,469,964 A | 11/1995 | Bailey | | |
| 5,597,530 A * | 1/1997 | Smith et al. | | 422/28 |
| 5,884,457 A * | 3/1999 | Ortiz et al. | | 53/468 |
| 6,164,044 A * | 12/2000 | Porfano et al. | | 53/471 |
| 6,189,195 B1 * | 2/2001 | Reilly et al. | | 29/434 |
| 6,263,641 B1 * | 7/2001 | Odell et al. | | 53/425 |
| 6,742,246 B2 * | 6/2004 | Stroup | | 29/823 |
| 7,392,638 B2 * | 7/2008 | Baldwin et al. | | 53/471 |
| 2006/0219317 A1 * | 10/2006 | Baldwin et al. | | 141/130 |

* cited by examiner

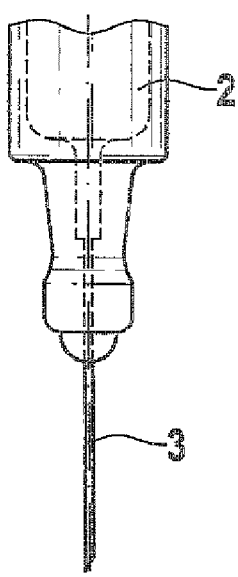
Fig. 2
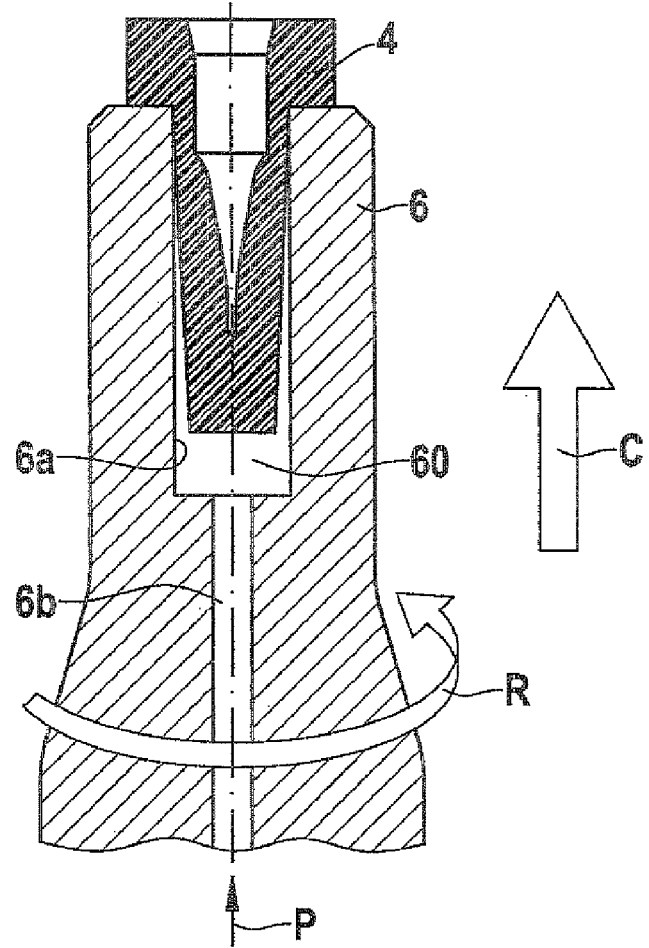

DEVICE AND METHOD FOR MOUNTING A NEEDLE GUARD ON A SYRINGE BODY

CROSS-REFERENCE TO RELATED APPLICATION

This application is a 35 USC 371 application of PCT/EP2007/059314 filed on Sep. 6, 2007.

BACKGROUND OF THE INVENTION

1. Field of the Invention

The present invention relates to a device for mounting a needle guard on a syringe body and to a method for mounting a needle guard on a syringe body.

2. Description of the Prior Art

From the prior art, various devices are known for delivering closures, especially for pharmaceutical containers. Such devices for instance include a vibration-promoting cup, which orients the closures and dispenses them into a feeder groove. The closures are delivered to a closing wheel, which takes the individual closures from the feeder groove and upon its further rotation sets them on bottles and then closes them.

One such device is known for instance from German Patent Disclosure DE 103 22 476 A1. In it, a sorting device and the feeder groove are coupled to one another and movable jointly as a unit. In particular upon closure of a syringe provided with a needle and a needle guard, however, a situation can often occur in the prior art in which the needle guard is put in place skewed, so that the needle of the syringe touches the needle guard and might become bent, or that the needle pierces the needle guard. It can also happen that the closure is not placed on the syringe with the requisite placement force.

ADVANTAGES AND SUMMARY OF THE INVENTION

The device according to the invention for mounting a needle guard on a syringe body has the advantage over the prior art that the needle guard can be placed on the syringe body quickly and securely, without contact occurring between the needle guard and a needle of the syringe body. As a result, it is possible in particular to use syringe bodies that have glued-on needles, which are especially vulnerable to being touched by the needle guard. The device according to the invention includes a retainer for retaining the syringe body, a needle guard receptacle for receiving the needle guard, and a compressed-air device for furnishing compressed air. The device further includes a first displacement device for moving the needle guard receptacle in the vertical direction and a rotation device for at least partially rotating the needle guard receptacle during the vertical displacement. The needle guard receptacle is disposed below the retainer, so that the placement of the needle guard on the syringe body is done from below. The compressed air is delivered to the needle guard receptacle in such a way that the needle guard floats on an air cushion in the needle guard receptacle and rotates and thus is simple to place centrally on the syringe body.

Preferably, the device further includes a holding-down device, which is disposed above the retainer of the syringe body. The holding-down device can be put into contact with the other end of the syringe body and furnishes a counterforce to the placement force for placement of the needle guard on the syringe body.

The holding-down device is preferably movable in the vertical direction by means of a second displacement device.

As a result, it is possible for the holding-down device and the needle guard receptacle to be moved preferably simultaneously in opposite directions, for placement of the needle guard on the syringe body.

Also preferably, the device of the invention includes a force sensor, for picking up a force of the placement of the needle guard on the syringe body. The use of the force sensor makes it possible to determine, from the placement force, whether the needle guard has been placed correctly and securely on the syringe body. As a result, as soon as the needle guard is put in place, syringes that have a needle guard placed with too great or too little placement force can be rejected.

The first sensor is preferably disposed on the holding-down device. As a result, an especially compact construction can be assured.

The device according to the invention further preferably includes a control device with a memory, and in the memory, at least one predetermined force value for the placement force is stored. The control device serves to compare a picked-up placement force with the predetermined placement force and if needed to reject the syringe if the placement force is wrong. It should be noted that both a lower limit for the placement force and an upper limit for the placement force can be monitored here.

Especially preferably, the first displacement device and the second displacement device are activated simultaneously. As a result, an especially short time for placing the needle guard on the syringe body can be assured. [in other words, it can be assured that it is especially fast]

The invention further relates to a method for mounting a needle guard on a syringe body, which includes the steps of retaining the syringe body by means of a retainer and inserting the needle guard into a needle guard receptacle. The needle guard receptacle is disposed below the syringe body. Moreover, compressed air is furnished, which is delivered to the needle guard receptacle in order to put the needle guard in the needle guard receptacle into a state in which it floats on an air cushion. If the needle guard is in the floating state, then the placement of the needle guard on the syringe body is accomplished by moving the needle guard receptacle vertically in the direction toward the syringe body, and during the placement operation, the needle guard receptacle executes a rotary motion. As a result, secure centering of the needle guard receptacle on the syringe body is achieved.

The method furthermore preferably includes the picking up of a placement force of the needle guard on the syringe body, especially so that syringes with incorrectly placed needle guards will be rejected. A syringe is rejected particularly whenever the placement force is less or greater than a predetermined value.

BRIEF DESCRIPTION OF THE DRAWINGS

A preferred exemplary embodiment of the invention is described in detail below in conjunction with the accompanying drawings. In the drawings:

FIG. 2 is an enlarged view, partly in section, of the device of FIG. 1 during the placement operation;

DESCRIPTION OF THE PREFERRED EMBODIMENT

Below, in conjunction with FIGS. 1 through 4, a device 1 for mounting a needle guard 4 on a syringe body 2 will be described in detail.

Figure 1:
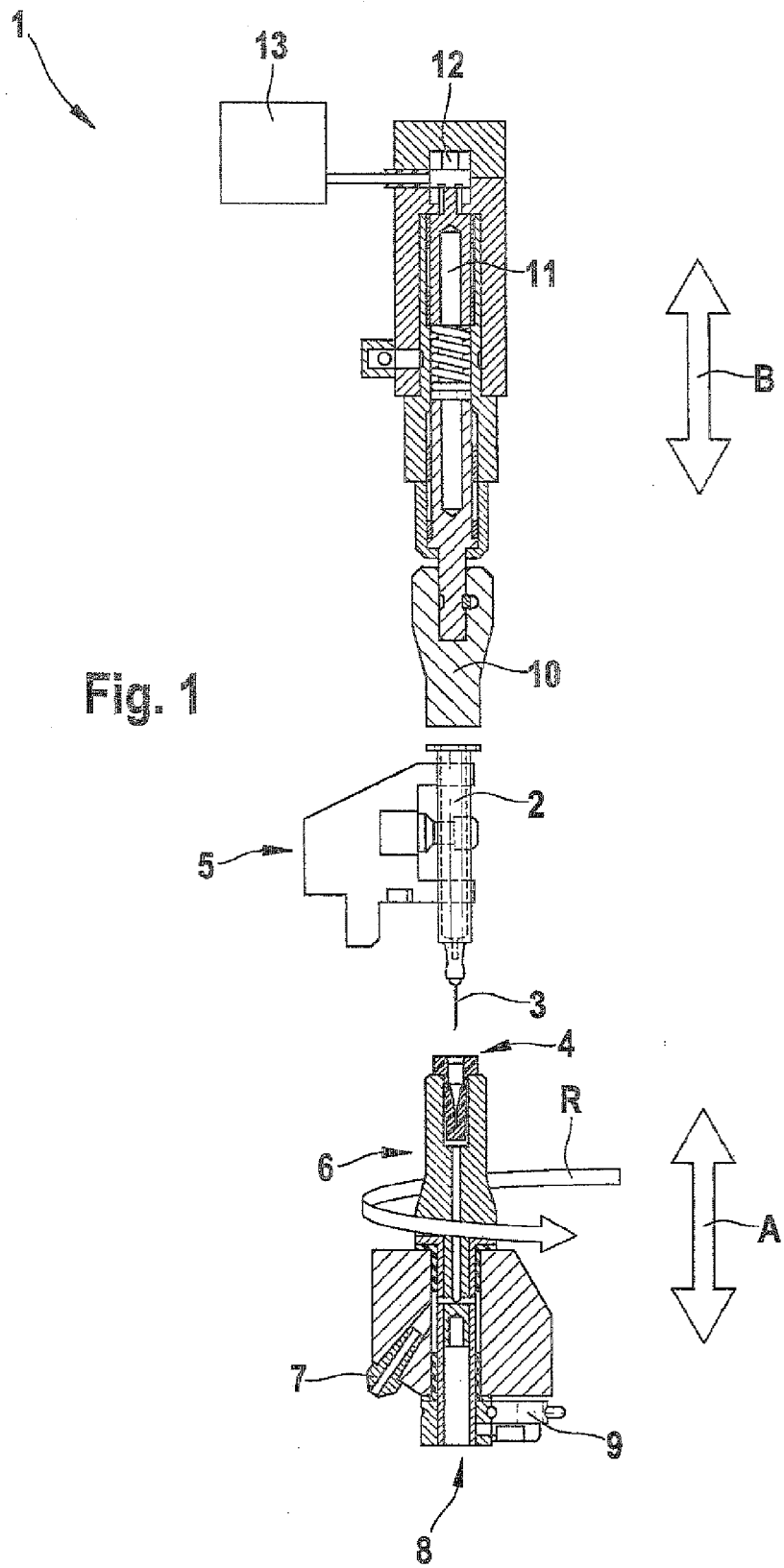
FIG. 1 is a schematic sectional view of a device for mounting a needle guard on a syringe body.

FIG. 1 schematically shows the overall construction of the device 1. The device 1 includes a retainer 5 for retaining the syringe body 2. The retainer 5 may for instance be a gripping unit or the like. The device 1 furthermore includes a needle guard receptacle 6 and a holding-down device 10. As indicated by the double arrow A in FIG. 1, the needle guard receptacle 6 can be moved vertically up and down in the direction of the retainer 5. Moreover, the needle guard receptacle can be rotated in the direction of the arrow R. The entire needle guard receptacle 6 is rotated and moved in the vertical direction. The rotation is done over a predetermined angle, such as 90°. The needle guard receptacle 6 is moved in the vertical direction by means of a first displacement device 8. The first displacement device 8 is for instance a pressure-fluid-actuated piston. The rotation in the direction of the arrow R can be furnished by means of a rotation device 9. The holding-down device 10, as indicated by the double arrow B, can also be moved up and down in the vertical direction. The motion of the holding-down device 10 is effected by means of a second displacement device 11, which is for example a spring-loaded piston or the like. The piston can be actuated by pressure fluid, and once the supply of pressure fluid is withdrawn, an automated restoration takes place by means of a prestressed spring.

The device 1 further includes a compressed-air device 7, for furnishing compressed air to the needle guard receptacle 6. The needle guard receptacle 6 includes an essentially cup-shaped receptacle 6a, which has an opening on its bottom that communicates with a compressed air delivery conduit 6b. This can be seen in FIG. 2. As indicated by the arrow P in FIG. 2, compressed air is delivered to the cup-shaped receptacle 6a through the compressed air delivery conduit 6b. As a result, an air cushion 60 is created in the cup-shaped receptacle 6a, and the needle guard 4 is kept floating on it.

A force measuring sensor 12 is also disposed on the holding-down device 10. The force measuring sensor 12 serves to pick up a placement force, with which the needle guard 4 is placed on the syringe body 2. The force sensor 12 is connected to a control device 13. The control device 13 includes a memory, in which predetermined upper and lower limit values for the placement force are stored. The control device 13 compares the actual value of the placement force with the values stored in memory and as needed, if there is a deviation, outputs a signal accordingly and rejects the syringes with incorrectly placed needle guards.

The function of the device 1 of the invention is as follows: In a first step, a syringe body 2, on which a needle 3 has been placed, is retained by the retainer 5. The needle 3 can be secured to the syringe body 2 by adhesive bonding, for instance. Simultaneously or immediately afterward, a needle guard 4 is inserted in the needle guard receptacle 6, or more precisely into the cup-shaped receptacle 6a. This can be effected by means of a feeder groove, for instance. The needle guard receptacle 6 and the holding-down device 10 are located in their outset positions. This situation is shown schematically in FIG. 1. Now, if the needle guard 4 is to be placed on the placement force 2, then first compressed air is generated by means of the compressed-air device 7 or withdrawn from a compressed air reservoir and delivered to the lower region of the cup-shaped receptacle 6a via the compressed air delivery conduit 6b. This creates an air cushion 60, on which the needle guard 4 floats. This situation is shown in FIG. 2. In a next step, the needle guard receptacle 6 is moved in the vertical direction upward in the direction toward the syringe body 2. This is indicated by the arrow C in FIG. 2. Simultaneously, a rotation of the needle guard receptacle 6 takes place about a predetermined angle, such as 90°. The rotation thus takes place simultaneously with the vertical motion of the needle guard receptacle 6.

Figure 3:
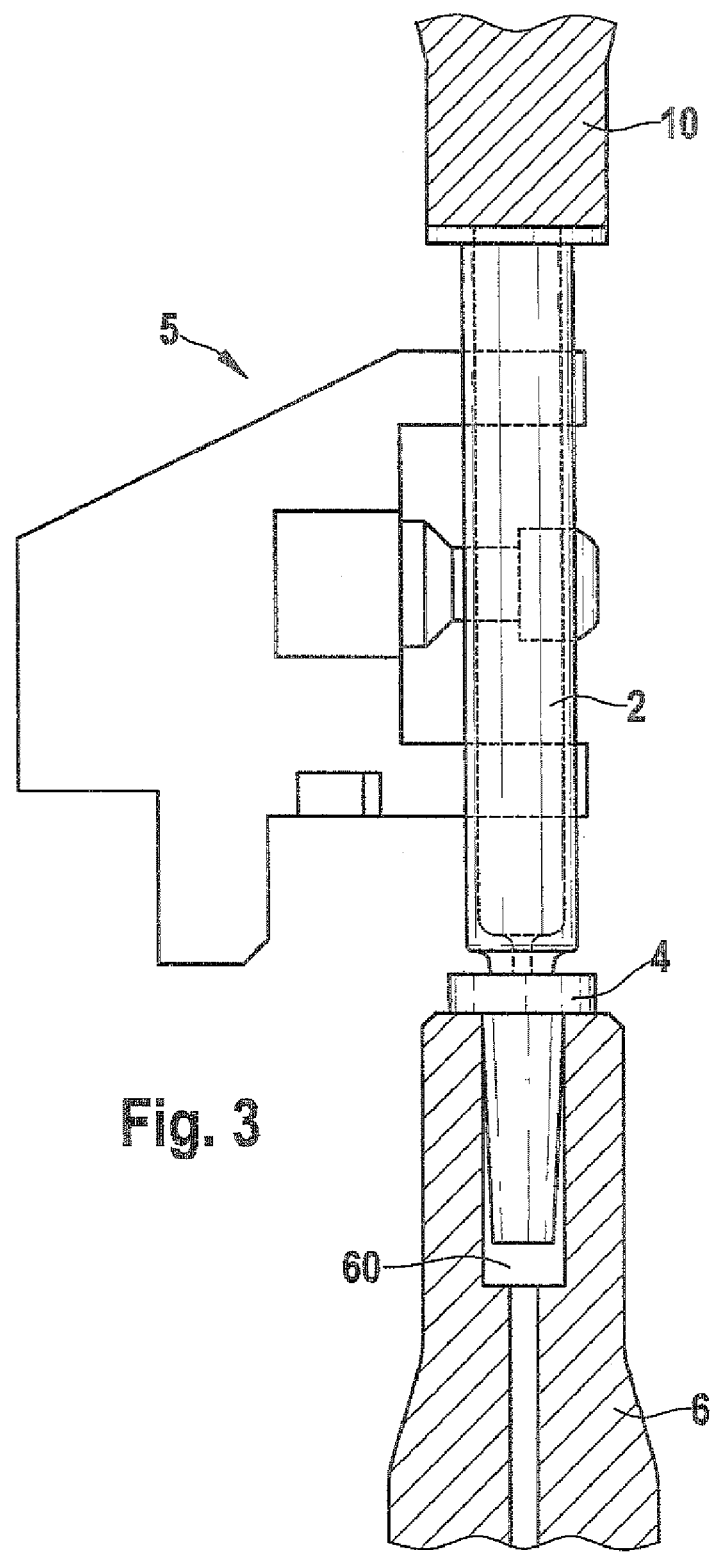
FIG. 3 is a schematic view, partly in section, of the device once the needle guard has been placed.

While the needle guard receptacle 6 is moving upward in the direction of the syringe body 2, the holding-down device 10 simultaneously moves vertically downward. The holding-down device 10 is moved until such time as it comes into contact with the back end of the syringe body 2, in order to furnish a resistance upon placement of the needle guard 4 on the syringe body 2. The holding-down device 10 must already rest on the opposite end of the syringe body 2 before the actual operation of placing the needle guard 4, so as to furnish the placement resistance. The needle guard receptacle 6 is moved onward in the direction of the syringe body 2, until the needle guard 4 comes into contact with a preferably tapering region of the syringe body 2 above the needle guard as seen in FIG. 3. By means of the air cushion 60 and the rotary motion R, the needle guard 4 is centered. The placement of the needle guard 4 thus takes place with a placement force that is picked up by the force measuring sensor 12 on the other end of the holding-down device 10. The force measuring sensor 12 sends the picked-up placement force onward to the control device 13, which compares the actual placement force with a placement force stored in memory. If there is a predetermined deviation, then the control device 13 outputs a signal accordingly, and the syringe body having the wrongly placed needle guard is rejected.

Figure 4:
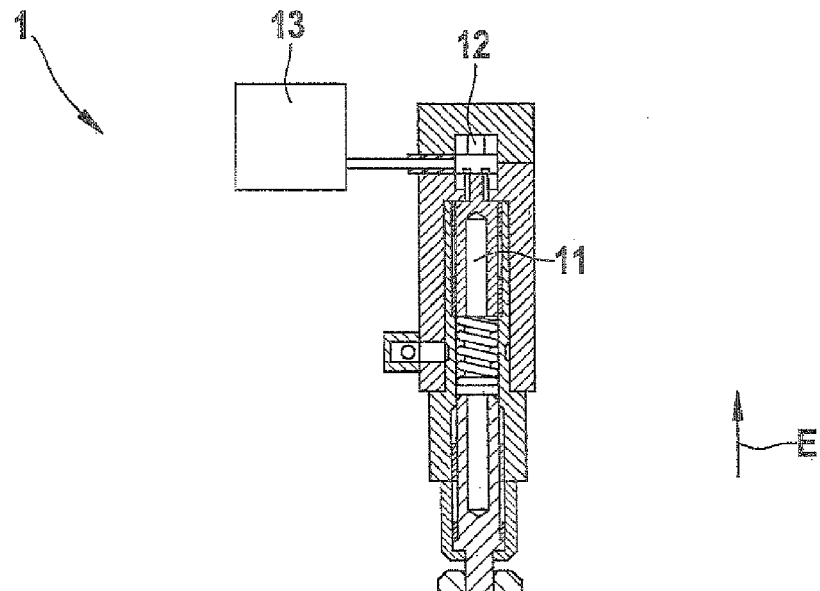
FIG. 4 is a schematic view, partly in section, of the device which has been returned to its outset state.
Figure 4:
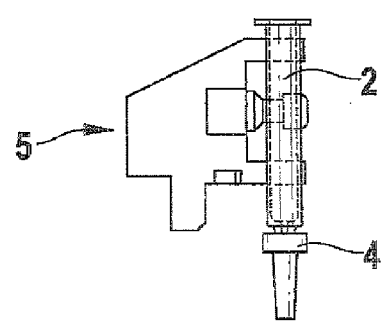
Figure 4:
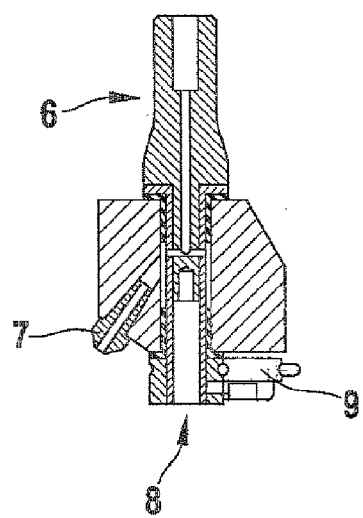

Once the needle guard 4 has been placed on the syringe body 2, the needle guard receptacle 6 and the holding-down device 10 are simultaneously moved in opposite directions again; that is, the needle guard receptacle 6 is moved downward, as indicated in FIG. 4 by the arrow D, and the holding-down device 10 is moved upward, as indicated in FIG. 4 by the arrow E.

The placement of the needle guard 4 on the syringe body 2 is thus concluded, and the retainer 5 can carry the syringe body, provided with the needle guard, away or transfer it to a suitable conveyor device.

According to the invention, the needle guard 4 is thus placed on the syringe body 2 from below, and the needle guard 4 floats on an air cushion 60. As a result, secure centering of the needle guard 4 during the placement operation is assured. This is additionally reinforced by the rotation of the needle guard receptacle 6 during the placement. The placement force is monitored by means of the force measuring sensor 12, so that the device 1 can immediately reject incorrectly placed syringes. As a result, syringes with an incorrectly or poorly placed needle guard can in particular be prevented from being distributed.

The foregoing relates to the preferred exemplary embodiment of the invention, it being understood that other variants and embodiments thereof are possible within the spirit and scope of the invention, the latter being defined by the appended claims.

The invention claimed is:

1. A device for mounting a needle guard on a syringe body which is provided with a needle, comprising:
   a retainer retaining the syringe body;
   a needle guard receptacle receiving the needle guard;
   a compressed-air device furnishing compressed air;

a first displacement device moving the needle guard receptacle in a longitudinal direction with respect to the syringe body; and a rotation device for at least partially rotating the needle guard receptacle, wherein the needle guard receptacle is disposed below the retainer in the longitudinal direction, wherein the compressed air is supplied to the needle guard receptacle in such a way that the needle guard is held floating on an air cushion, and the needle guard receptacle is movable in the longitudinal direction by means of the first displacement device.

2. The device as defined by claim 1, further comprising a holding-down device, which is disposed above the retainer and is put into contact with an end, remote from the needle guard, of the syringe body.

3. The device as defined by claim 2, wherein the holding-down device is movable in a vertical direction by means of a second displacement device.

4. The device as defined by claim 3, further comprising a force measuring sensor which picks up a placement force during placement of the needle guard on the syringe body.

5. The device as defined by claim 2, further comprising a force measuring sensor which picks up a placement force during placement of the needle guard on the syringe body.

6. The device as defined by claim 4, wherein the force measuring sensor is disposed on the holding-down device.

7. The device as defined by claim 5, wherein the force measuring sensor is disposed on the holding-down device.

8. The device as defined by claim 4, further comprising a control device with a memory, and in the memory at least one predetermined value for the placement force is stored, and the control device compares a picked-up value of the placement force with a predetermined value for the placement force.

9. The device as defined by claim 5, further comprising a control device with a memory, and in the memory at least one predetermined value for the placement force is stored, and the control device compares a picked-up value of the placement force with a predetermined value for the placement force.

10. The device as defined by claim 6, further comprising a control device with a memory, and in the memory at least one predetermined value for the placement force is stored, and the control device compares a picked-up value of the placement force with a predetermined value for the placement force.

11. The device as defined by claim 7, further comprising a control device with a memory, and in the memory at least one predetermined value for the placement force is stored, and the control device compares a picked-up value of the placement force with a predetermined value for the placement force.

12. The device as defined by claim 3, wherein the first displacement device and the second displacement device are simultaneously activatable.

13. The device as defined by claim 4, wherein the first displacement device and the second displacement device are simultaneously activatable.

14. The device as defined by claim 6, wherein the first displacement device and the second displacement device are simultaneously activatable.

15. The device as defined by claim 8, wherein the first displacement device and the second displacement device are simultaneously activatable.

16. A method for mounting a needle guard on a syringe body, including the steps of:
   retaining the syringe body by means of a retainer;
   inserting the needle guard into a needle guard receptacle, the needle guard receptacle being disposed below the syringe body with respect to a longitudinal axis of the syringe body;
   furnishing compressed air in the needle guard receptacle, in order to put the needle guard in the needle guard receptacle in a floating state on an air cushion;
   moving the needle guard receptacle toward the syringe body, in order to place the needle guard on the syringe body, and simultaneously rotating the needle guard receptacle.

17. The method as defined by claim 16, wherein a placement force during placement of the needle guard on the syringe body is measured by means of a force sensor.

18. The method as defined by claim 17, wherein if the placement force has a predetermined deviation from a predetermined placement force, the syringe body is rejected.

* * * * *